US008874232B2

(12) United States Patent
Chen

(10) Patent No.: US 8,874,232 B2
(45) Date of Patent: Oct. 28, 2014

(54) ELECTRODE ARRAY HAVING CONCENTRIC SPLIT RING ELECTRODES AND METHODS OF MAKING THE SAME

(75) Inventor: Roger Chen, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 7 days.

(21) Appl. No.: 12/946,687

(22) Filed: Nov. 15, 2010

(65) Prior Publication Data
US 2011/0130818 A1  Jun. 2, 2011

Related U.S. Application Data

(60) Provisional application No. 61/265,243, filed on Nov. 30, 2009.

(51) Int. Cl.
*A61N 1/00* (2006.01)
*A61N 1/05* (2006.01)

(52) U.S. Cl.
CPC ............ *A61N 1/0534* (2013.01); *A61N 1/0539* (2013.01)
USPC ............ 607/116; 607/117; 607/118; 607/122

(58) Field of Classification Search
CPC ......... A61N 1/05; A61N 1/044; A61N 1/048; A61N 1/0424; A61N 1/0529; A61N 1/0531; A61N 1/0534
See application file for complete search history.

(56) References Cited

U.S. PATENT DOCUMENTS

| | | | |
|---|---|---|---|
| 4,602,624 A | | 7/1986 | Naples et al. |
| 4,630,611 A | | 12/1986 | King |
| 4,744,370 A | | 5/1988 | Harris |
| 5,000,194 A | * | 3/1991 | van den Honert et al. ..... 607/137 |
| 5,135,001 A | | 8/1992 | Sinofsky et al. |
| 5,374,285 A | | 12/1994 | Vaiani et al. |
| 5,458,629 A | | 10/1995 | Baudino et al. |

(Continued)

FOREIGN PATENT DOCUMENTS

| | | |
|---|---|---|
| EP | 0580928 A1 | 2/1994 |
| EP | 0650694 B1 | 7/1998 |

(Continued)

OTHER PUBLICATIONS

U.S. Appl. No. 13/275,112, filed Oct. 17, 2011.

(Continued)

*Primary Examiner* — Michael Kahelin
*Assistant Examiner* — Mallika D Fairchild
(74) *Attorney, Agent, or Firm* — Lowe Graham Jones PLLC; Bruce E. Black

(57) ABSTRACT

A device for brain stimulation includes a lead body having a longitudinal surface and a distal end. The device further includes at least one ring array. The at least one ring array includes a plurality of split ring electrodes disposed on the distal end of the lead body. Each of the plurality of split ring electrodes includes a stimulating portion and a base portion coupled to the stimulating portion. The split ring electrodes of the at least one ring array are arranged about the circumference of the lead body. At least a portion of the base portion of at least one of the plurality of split ring electrodes is disposed below, and insulated from, at least a portion of the stimulating portion of another of the plurality of split electrodes.

20 Claims, 10 Drawing Sheets

(56) References Cited

U.S. PATENT DOCUMENTS

| | | |
|---|---|---|
| 5,522,874 A | 6/1996 | Gates |
| 5,711,316 A | 1/1998 | Elsberry et al. |
| 5,713,922 A | 2/1998 | King |
| 5,800,350 A | 9/1998 | Coppleson et al. |
| 5,843,148 A | 12/1998 | Gijsbers et al. |
| 5,938,688 A | 8/1999 | Schiff |
| 5,987,361 A | 11/1999 | Mortimer |
| 6,018,684 A | 1/2000 | Bartig et al. |
| 6,134,478 A | 10/2000 | Spehr |
| 6,161,047 A | 12/2000 | King et al. |
| 6,167,311 A | 12/2000 | Rezai |
| 6,322,559 B1 | 11/2001 | Daulton et al. |
| 6,510,347 B2 | 1/2003 | Borkan |
| 6,556,873 B1 | 4/2003 | Smits |
| 6,564,078 B1 | 5/2003 | Marino et al. |
| 6,678,564 B2 | 1/2004 | Ketterl et al. |
| 6,757,970 B1 | 7/2004 | Kuzma et al. |
| 7,027,852 B2 | 4/2006 | Helland |
| 7,047,084 B2 | 5/2006 | Erickson et al. |
| 7,292,890 B2 | 11/2007 | Whitehurst et al. |
| 7,489,971 B1 | 2/2009 | Franz |
| 7,668,601 B2 | 2/2010 | Hegland et al. |
| 7,761,985 B2 | 7/2010 | Hegland et al. |
| 7,809,446 B2 | 10/2010 | Meadows |
| 7,840,188 B2 | 11/2010 | Kurokawa |
| 7,848,802 B2 | 12/2010 | Goetz |
| 7,856,707 B2 | 12/2010 | Cole |
| 7,860,570 B2 | 12/2010 | Whitehurst et al. |
| 7,974,705 B2 | 7/2011 | Zdeblick et al. |
| 7,979,140 B2 | 7/2011 | Schulman |
| 8,000,808 B2 | 8/2011 | Hegland et al. |
| 8,019,440 B2 | 9/2011 | Kokones et al. |
| 8,036,755 B2 | 10/2011 | Franz |
| 8,041,309 B2 | 10/2011 | Kurokawa |
| 8,099,177 B2 | 1/2012 | Dahlberg |
| 8,225,504 B2 | 7/2012 | Dye et al. |
| 8,295,944 B2 | 10/2012 | Howard et al. |
| 8,321,025 B2 | 11/2012 | Bedenbaugh |
| 8,583,237 B2 | 11/2013 | Bedenbaugh |
| 2002/0156513 A1 | 10/2002 | Borkan |
| 2002/0183817 A1 | 12/2002 | Van Venrooij et al. |
| 2005/0015130 A1 | 1/2005 | Gill |
| 2005/0038489 A1 | 2/2005 | Grill |
| 2005/0171587 A1 | 8/2005 | Daglow et al. |
| 2006/0025841 A1 | 2/2006 | McIntyre |
| 2006/0247697 A1 | 11/2006 | Sharma et al. |
| 2007/0203546 A1 | 8/2007 | Stone et al. |
| 2008/0103580 A1 | 5/2008 | Gerber |
| 2008/0114230 A1 | 5/2008 | Addis |
| 2008/0215125 A1 | 9/2008 | Farah et al. |
| 2009/0204192 A1 | 8/2009 | Carlton et al. |
| 2009/0204193 A1* | 8/2009 | Kokones et al. ............... 607/116 |
| 2010/0036468 A1 | 2/2010 | Decre et al. |
| 2010/0076535 A1 | 3/2010 | Pianca et al. |
| 2010/0082076 A1 | 4/2010 | Lee et al. |
| 2010/0094387 A1 | 4/2010 | Pianca et al. |
| 2010/0125310 A1 | 5/2010 | Wilson et al. |
| 2010/0268298 A1 | 10/2010 | Moffitt et al. |
| 2011/0005069 A1 | 1/2011 | Pianca |
| 2011/0047795 A1 | 3/2011 | Turner et al. |
| 2011/0056076 A1 | 3/2011 | Hegland et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0131808 A1 | 6/2011 | Gill |
| 2011/0238129 A1 | 9/2011 | Moffitt et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0317587 A1 | 11/2013 | Barker |
| 2013/0325091 A1 | 12/2013 | Pianca et al. |

FOREIGN PATENT DOCUMENTS

| | | |
|---|---|---|
| EP | 0832667 B1 | 2/2004 |
| EP | 1181947 B1 | 1/2006 |
| EP | 2092952 A1 | 8/2009 |
| WO | 9732628 A1 | 9/1997 |
| WO | 9955411 A3 | 2/2000 |
| WO | 0038574 A1 | 7/2000 |
| WO | 02068042 A1 | 9/2002 |
| WO | 2004045707 A1 | 6/2004 |
| WO | 2008053789 A1 | 5/2008 |
| WO | 2009025816 A1 | 2/2009 |
| WO | 2009102536 A1 | 8/2009 |

OTHER PUBLICATIONS

U.S. Appl. No. 13/363,059, filed Jan. 31, 2012.
U.S. Appl. No. 13/368,982, filed Feb. 8, 2012.
U.S. Appl. No. 13/369,013, filed Feb. 8, 2012.
U.S. Appl. No. 13/368,733, filed Feb. 8, 2012.
U.S. Appl. No. 13/951,057, filed Jul. 25, 2013.
U.S. Appl. No. 14/053,112, filed Oct. 14, 2013.
U.S. Appl. No. 13/899,316, filed May 21, 2013.
U.S. Appl. No. 13/750,725, filed Jan. 25, 2013.
U.S. Appl. No. 13/787,171, filed Mar. 6, 2013.

* cited by examiner

ELECTRODE ARRAY HAVING CONCENTRIC SPLIT RING ELECTRODES AND METHODS OF MAKING THE SAME

CROSS-REFERENCE TO RELATED APPLICATIONS

This application claims the benefit under 35 U.S.C. §119 (e) of U.S. Provisional Patent Application Ser. No. 61/265,243 filed on Nov. 30, 2009, which is incorporated herein by reference.

FIELD

The invention is directed to devices and methods for brain stimulation including deep brain stimulation. In addition, the invention is directed to devices and method for brain stimulation using a lead having concentric split ring electrodes.

BACKGROUND

Deep brain stimulation can be useful for treating a variety of conditions including, for example, Parkinson's disease, dystonia, essential tremor, chronic pain, Huntington's Disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging (MRI) or computerized tomography (CT) scans can provide a starting point for determining where the stimulating electrode should be positioned to provide the desired stimulus to the target neurons.

Upon insertion, current is introduced along the length of the lead to stimulate target neurons in the brain. This stimulation is provided by electrodes, typically in the form of rings, disposed on the lead. The current projects from each electrode similarly and in all directions at any given length along the axis of the lead. Because of the shape of the electrodes, radial selectivity of the current is minimal. This results in the unwanted stimulation of neighboring neural tissue, undesired side effects and an increased duration of time for the proper therapeutic effect to be obtained.

In the field of deep brain stimulation, radially segmented electrode arrays (RSEA) have been developed to provide superior radial selectivity of current. Radially segmented electrode arrays are useful for deep brain stimulation because the target structures in the deep brain are often not symmetric about the axis of the distal electrode array. In some cases, a target may be located on one side of a plane running through the axis of the lead. In other cases, a target may be located at a plane that is offset at some angle from the axis of the lead. Thus, radially segmented electrode arrays may be useful for selectively simulating tissue. These radially segmented arrays may be made using concentric split ring electrodes.

BRIEF SUMMARY

In one embodiment, a device for brain stimulation includes a lead body having a longitudinal surface and a distal end. The device further includes at least one ring array. The at least one ring array includes a plurality of split ring electrodes disposed on the distal end of the lead body. Each of the plurality of split ring electrodes includes a stimulating portion and a base portion coupled to the stimulating portion. The split ring electrodes of the at least one ring array are arranged about the circumference of the lead body. At least a portion of the base portion of at least one of the plurality of split ring electrodes is disposed below, and insulated from, at least a portion of the stimulating portion of another of the plurality of split electrodes.

In another embodiment, a device for brain stimulation includes a lead body having a longitudinal surface and a distal end. The device further includes a plurality of split ring electrodes disposed on the distal end of the lead body. Each of the plurality of split ring electrodes includes a stimulating portion and a base portion coupled to the stimulating portion. The split ring electrodes are arranged such that the base portions are arranged around an inner circle having a first radius and the stimulating portions are arranged around an outer circle having a second radius, wherein the first radius is less than the second radius.

In yet another embodiment, a method of manufacturing a device for brain stimulation includes forming a lead body having a longitudinal surface and a distal end. At least one ring array is formed. The at least one ring array includes a plurality of split ring electrodes at the distal end of the lead body. Each of the plurality of split ring electrodes includes a stimulating portion and a base portion coupled to the stimulating portion. The split ring electrodes of the at least one ring array are arranged about the circumference of the lead body. At least a portion of the base portion of at least one of the plurality of split ring electrodes is disposed below and insulated from, at least a portion of the stimulating portion of another of the plurality of split electrodes.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of devices and methods for brain stimulation including deep brain stimulation. In addition, the invention is directed to devices and method for brain stimulation using a lead having a plurality of split ring electrodes arranged in a ring array.

A lead for deep brain stimulation may include stimulation electrodes, recording electrodes, or a combination of both. A practitioner may determine the position of the target neurons using the recording electrode(s) and then position the stimulation electrode(s) accordingly without removal of a recording lead and insertion of a stimulation lead. In some embodiments, the same electrodes can be used for both recording and stimulation. In some embodiments, separate leads can be used; one with recording electrodes which identify target neurons, and a second lead with stimulation electrodes that replaces the first after target neuron identification. A lead may include recording electrodes spaced around the circumference of the lead to more precisely determine the position of the target neurons. In at least some embodiments, the lead is rotatable so that the stimulation electrodes can be aligned with the target neurons after the neurons have been located using the recording electrodes.

Deep brain stimulation devices and leads are described in the art. See, for instance, U.S. Patent Publication 2006/0149335 A1 ("Devices and Methods For Brain Stimulation"), and co-pending patent application U.S. Ser. No. 12/237,888 ("Leads With Non-Circular-Shaped Distal Ends For Brain Stimulation Systems and Methods of Making and Using"). Each of these references is incorporated herein by reference in its respective entirety.

Figure 10:
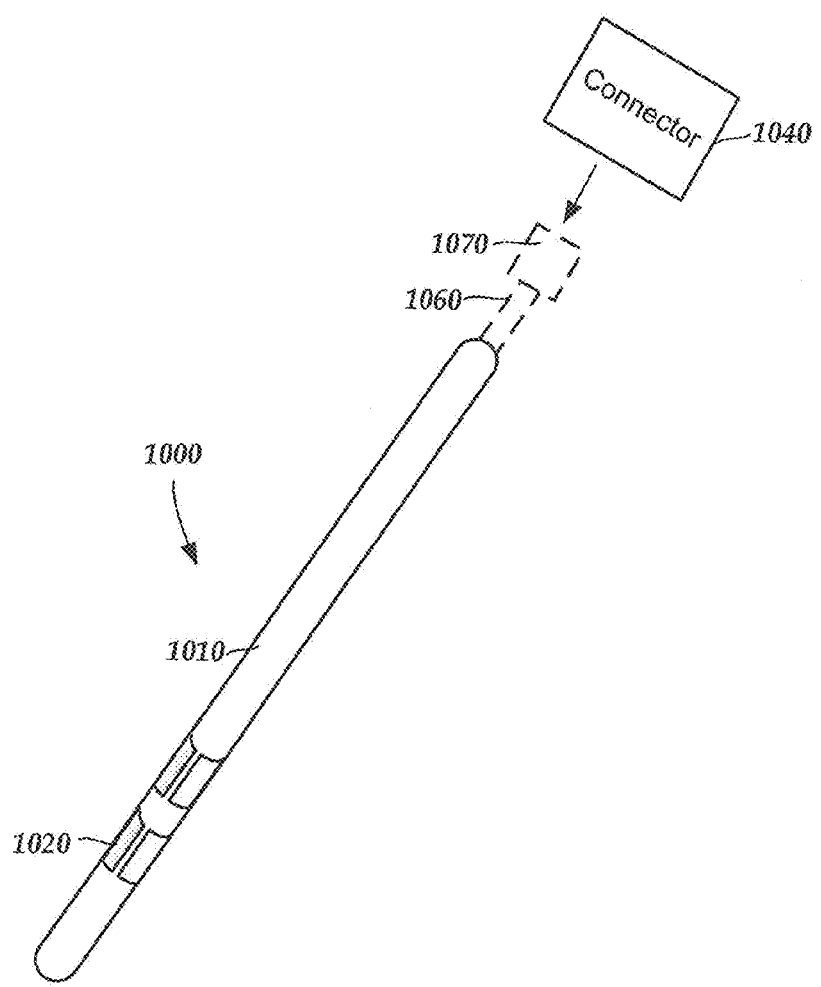
FIG. 10 is a schematic side view of one embodiment of a device for brain stimulation, according to the invention.

FIG. 10 illustrates one embodiment of a device for brain stimulation. The device includes a lead 100, segmented electrodes 1020, a connector 1040 for connection of the electrodes to a control unit, and a stylet 1050 for assisting in insertion and positioning of the lead in the patient's brain. The stylet 1050 can be made of a rigid material. Examples of suitable materials include tungsten, stainless steel, or plastic. The stylet 1050 may have a handle 1060 to assist insertion into the lead, as well as rotation of the stylet 1050 and lead 100.

In one example of operation, access to the desired position in the brain can be accomplished by drilling a hole in the patient's skull or cranium with a cranial drill (commonly referred to as a burr), and coagulating and incising the dura mater, or brain covering. The lead 100 can be inserted into the cranium and brain tissue with the assistance of the stylet 1050. The lead can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): rotate the lead, insert the lead, or retract the lead. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The lead 100 for deep brain stimulation can include stimulation electrodes, recording electrodes, or both. In at least some embodiments, the lead is rotatable so that the stimulation electrodes can be aligned with the target neurons after the neurons have been located using the recording electrodes.

Stimulation electrodes may be disposed on the circumference of the lead to stimulate the target neurons. Stimulation electrodes may be ring-shaped so that current projects from each electrode equally in every direction at any given length along the axis of the lead. To achieve current steering, segmented electrodes can be utilized additionally or alternatively. Though the following description discusses stimulation electrodes, it will be understood that all configurations of the stimulation electrodes discussed may be utilized in arranging recording electrodes as well.

Figure 1A:
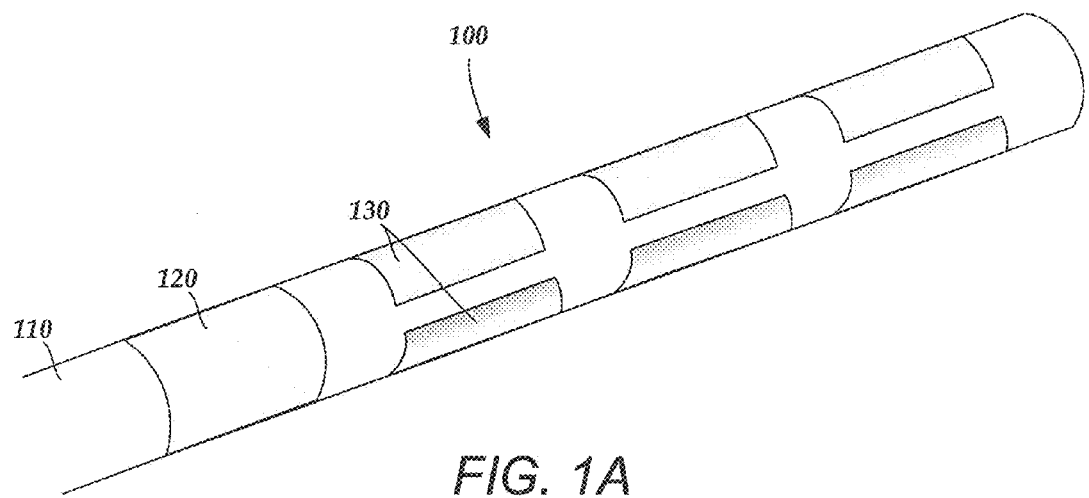
FIG. 1A is a schematic perspective view of one embodiment of a portion of a lead having a plurality of segmented electrodes and a ring electrode, according to the invention.

FIG. 1A illustrates one embodiment of a lead 100 for brain stimulation. The device includes a lead body 110, one or more ring electrodes 120, and a plurality of segmented electrodes 130. The lead body 110 can be formed of a biocompatible, non-conducting material such as, for example, a polymeric material. Suitable polymeric materials include, but are not limited to, silicone, polyethylene, polyurethanes, polyureas, or polyurethane-ureas. In at least some instances, the lead may be in contact with body tissue for extended periods of time. In at least some embodiments, the lead has a cross-sectional diameter of no more than 1.5 mm and may be in the range of 0.75 to 1.5 mm. In at least some embodiments, the lead has a length of at least 10 cm and the length of the lead may be in the range of 25 to 70 cm.

Stimulation electrodes may be disposed on the lead body 110. These stimulation electrodes may be made using a metal, alloy, conductive oxide, or any other suitable conductive material. Examples of suitable materials include, but are not limited to, platinum, iridium, platinum iridium alloy, stainless steel, titanium, or tungsten. Preferably, the stimulation electrodes are made of a material that is biocompatible and does not substantially corrode under expected operating conditions in the operating environment for the expected duration of use.

In at least some embodiments, any of the electrodes can be used as an anode or cathode and carry anodic or cathodic current. In some instances, an electrode might be an anode for a period of time and a cathode for a period of time. In other embodiments, the identity of a particular electrode or electrodes as an anode or cathode might be fixed.

The lead contains a plurality of segmented electrodes 130. Any number of segmented electrodes 130 may be disposed on the lead body 110. In some embodiments, the segmented electrodes 130 are grouped in sets of segmented electrodes, each set disposed around the circumference of the lead at or near a particular longitudinal position. The lead may have any number of sets of segmented electrodes. In at least some embodiments, the lead has one, two, three, four, five, six, seven, or eight sets of segmented electrodes. In at least some embodiments, each set of segmented electrodes contains the same number of segmented electrodes 130. In some embodiments, each set of segmented electrodes contains three segmented electrodes 130. In at least some other embodiments, each set of segmented electrodes contains two, four, five, six, seven or eight segmented electrodes. The segmented electrodes 130 may vary in size and shape. For example, in FIG. 1B, the segmented electrodes 130 are shown as portions of a ring or curved rectangular portions. In some other embodiments, the segmented electrodes 130 are curved square portions. The shape of the segmented electrodes 130 may also be substantially triangular, diamond-shaped, oval, circular or spherical. In some embodiments, the segmented electrodes 130 are all of the same size, shape, diameter, width or area or any combination thereof. In some embodiments, the segmented electrodes of each set (or even all segmented electrodes) may be identical in size and shape.

In at least some embodiments, each set of segmented electrodes 130 may be disposed around the circumference of the lead body 110 to form a substantially or approximately cylindrical shape around the lead body 110. The spacing of the segmented electrodes 130 around the circumference of the lead body 110 may vary. In at least some embodiments, equal spaces, gaps or cutouts are disposed between each segmented electrodes 130 around the circumference of the lead body 110. In other embodiments, the spaces, gaps or cutouts between segmented electrodes may differ in size or shape. In other embodiments, the spaces, gaps, or cutouts between segmented electrodes may be uniform for a particular set of segmented electrodes or for all sets of segmented electrodes. The segmented electrodes 130 may be positioned in irregular or regular intervals around the lead body 110.

Stimulation electrodes in the form of ring electrodes 120 may be disposed on any part of the lead body 110, usually near a distal end of the lead. FIG. 1A illustrates a portion of a lead having one ring electrode. Any number of ring electrodes may be disposed along the length of the lead body 110. For example, the lead body may have one ring electrode, two ring electrodes, three ring electrodes or four ring electrodes. In some embodiments, the lead will have five, six, seven or eight ring electrodes. Other embodiments do not include ring electrodes.

In some embodiments, the ring electrodes 120 are substantially cylindrical and wrap around the entire circumference of the lead body 110. In some embodiments, the outer diameter of the ring electrodes 120 is substantially equal to the outer diameter of the lead body 110. Furthermore, the width of ring electrodes 120 may vary according to the desired treatment and the location of the target neurons. In some embodiments the width of the ring electrode 120 is less than or equal to the diameter of the ring electrode 120. In other embodiments, the width of the ring electrode 120 is greater than the diameter of the ring electrode 120.

Conductors (not shown) that attach to or from the ring electrodes 120 and segmented electrodes 130 also pass through the lead body 110. These conductors may pass through the material of the lead or through a lumen defined by the lead. The conductors are presented at a connector for coupling of the electrodes to a control unit (not shown). In one embodiment, the stimulation electrodes correspond to wire conductors that extend out of the lead body 110 and are then trimmed or ground down flush with the lead surface. The conductors may be coupled to a control unit to provide stimulation signals, often in the form of pulses, to the stimulation electrodes.

Figure 1B:
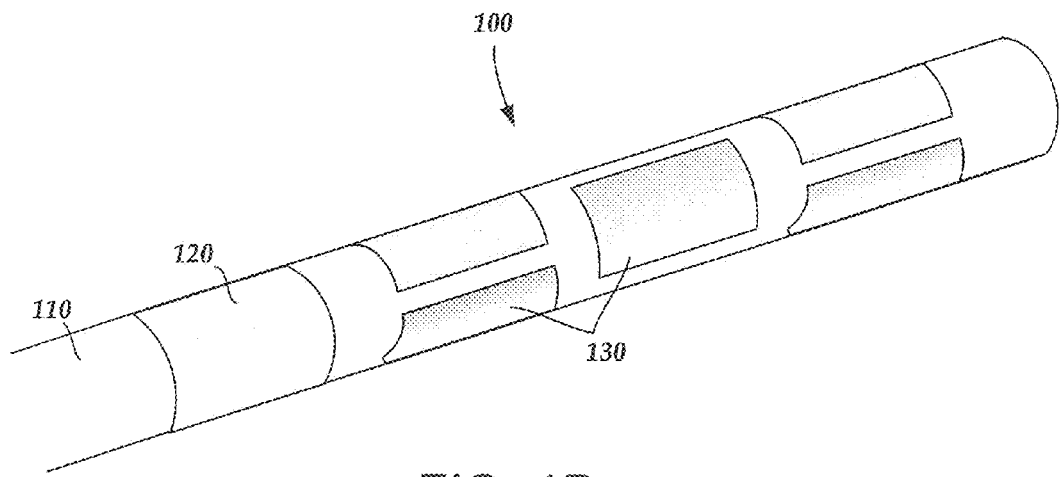
FIG. 1B is a schematic perspective view of another embodiment of a lead having a plurality of segmented electrodes arranged in staggered orientation and a ring electrode, according to the invention.

FIG. 1B is a schematic perspective view of another embodiment of a lead having a plurality of segmented electrodes. As seen in FIG. 1B, the plurality of segmented electrodes 130 may be arranged in different orientations relative to each other. In contrast to FIG. 1A, where the three sets of segmented electrodes are aligned along the length of the lead body 110, FIG. 1B displays another embodiment in which the three sets of segmented electrodes 130 are staggered. In at least some embodiments, the sets of segmented electrodes are staggered such that no segmented electrodes are aligned along the length of the lead body 110. In some embodiments, the segmented electrodes may be staggered so that at least one of the segmented electrodes is aligned with another segmented electrode of a different set, and the other segmented electrodes are not aligned.

Any number of segmented electrodes 130 may be disposed on the lead body 110 in any number of sets. FIGS. 1A and 1B illustrate embodiments including three sets of segmented electrodes. These three sets of segmented electrodes 130 may be disposed in different configurations. For example, three sets of segmented electrodes 130 may be disposed on the distal end of the lead body 110, distal to a ring electrode 120. Alternatively, three sets of segmented electrodes 130 may be disposed proximal to a ring electrode 120. By varying the location of the segmented electrodes 130, different coverage of the target neurons may be selected. For example, a specific configuration may be useful if the physician anticipates that the neural target will be closer to the distal tip of the lead body 110, while another arrangement may be useful if the physician anticipates that the neural target will be closer to the proximal end of the lead body 110. In at least some embodiments, the ring electrodes 120 alternate with sets of segmented electrodes 130.

Any combination of ring electrodes 120 and segmented electrodes 130 may be disposed on the lead. In some embodiments the segmented electrodes are arranged in sets. For example, a lead may include a first ring electrode 120, two sets of segmented electrodes, each set formed of three segmented electrodes 130, and a final ring electrode 120 at the end of the lead. This configuration may simply be referred to as a 1-3-3-1 configuration. It may be useful to refer to the electrodes with this shorthand notation. Other eight electrode configurations include, for example, a 2-2-2-2 configuration, where four sets of segmented electrodes are disposed on the lead, and a 4-4 configuration, where two sets of segmented electrodes, each having four segmented electrodes 130 are disposed on the lead. In some embodiments, the lead will have 16 electrodes. Possible configurations for a 16-electrode lead include, but are not limited to 4-4-4-4, 8-8, 3-3-3-3-3-1 (and all rearrangements of this configuration), and 2-2-2-2-2-2-2-2.

Figure 2:
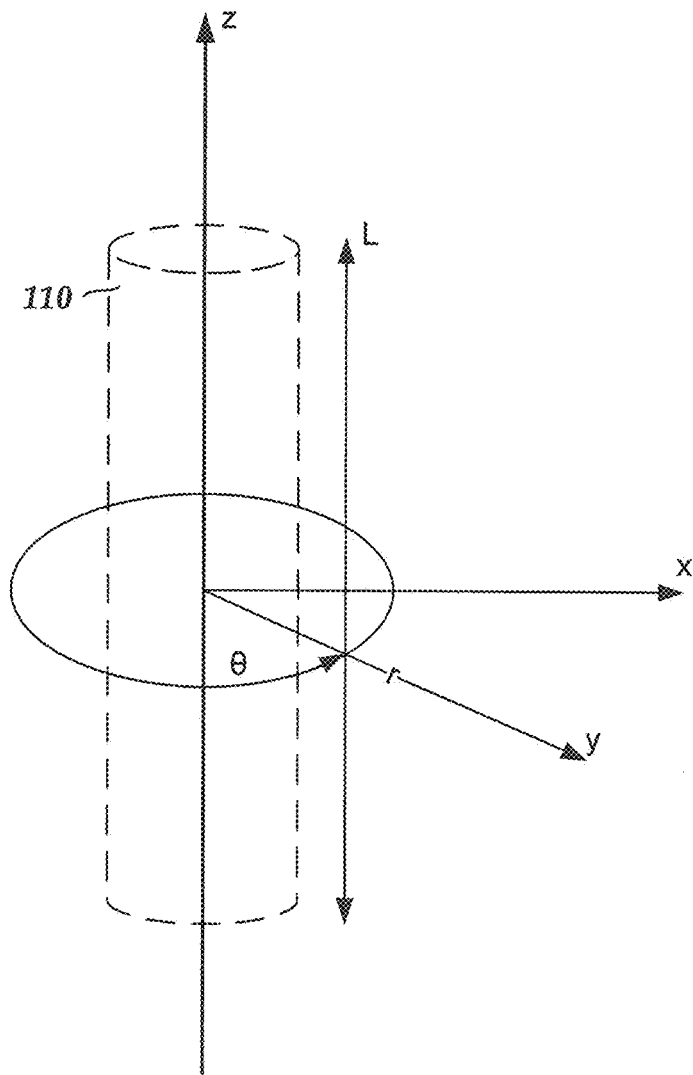
FIG. 2 is a schematic diagram of radial current steering along various electrode levels along the length of a lead, according to the invention.

FIG. 2 is a schematic diagram to illustrate radial current steering along various electrode levels along the length of a lead. While conventional lead configurations with ring electrodes are only able to steer current along the length of the lead (the z-axis), the segmented electrode configuration is capable of steering current in the x-axis, y-axis as well as the z-axis. Thus, the centroid of stimulation may be steered in any direction in the three-dimensional space surrounding the lead body 110. In some embodiments, the radial distance, r, and the angle θ around the circumference of the lead body 110 may be dictated by the percentage of anodic current (recognizing that stimulation predominantly occurs near the cathode, although strong anodes may cause stimulation as well)

introduced to each electrode as will be described in greater detail below. In at least some embodiments, the configuration of anodes and cathodes along the segmented electrodes 130 allows the centroid of stimulation to be shifted to a variety of different locations along the lead body 110.

As can be appreciated from FIG. 2, the centroid of stimulation can be shifted at each level along the length of the lead. The use of multiple sets of segmented electrodes 130 at different levels along the length of the lead allows for three-dimensional current steering. In some embodiments, the sets of segmented electrodes 130 are shifted collectively (i.e. the centroid of simulation is similar at each level along the length of the lead). In at least some other embodiments, each set of segmented electrodes 130 is controlled independently. Each set of segmented electrodes may contain two, three, four, five, six, seven, eight or more segmented electrodes. It will be understood that different stimulation profiles may be produced by varying the number of segmented electrodes at each level. For example, when each set of segmented electrodes includes only two segmented electrodes, uniformly distributed gaps (inability to stimulate selectively) may be formed in the stimulation profile. In some embodiments, at least three segmented electrodes 130 are utilized to allow for true 360° selectivity.

In addition to 360° selectivity, a lead having segmented electrodes may provide several advantages. First, the lead may provide for more directed stimulation, as well as less "wasted" stimulation (i.e. stimulation of regions other than the target region). By directing stimulation toward the target tissue, side effects may be reduced. Furthermore, because stimulation is directed toward the target site, the battery in an implantable pulse generator may last for a longer period of time between recharging.

As previously indicated, the foregoing configurations may also be used while utilizing recording electrodes. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrodes to further identify the target neurons and facilitate positioning of the stimulation electrodes. For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

Radially segmented electrode arrays may be manufactured in a variety of ways. In at least some embodiments, a plurality of split ring electrodes are used to form an array of radially segmented electrodes. The plurality of split ring electrodes may be modified to utilize different numbers of electrodes, to adjust the radial spacing between electrodes or to vary the longitudinal position between levels of electrodes.

Figure 3A:
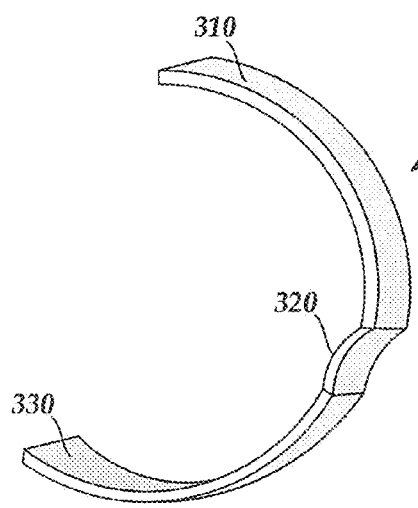
FIG. 3A is a schematic perspective view of one embodiment of a split ring electrode, according to the invention.

FIG. 3A is a schematic perspective view of one embodiment of a split ring electrode 300. As will be explained further below, the shape and size of the split ring electrode 300 may be modified. The split ring electrode 300 of FIG. 3A includes a stimulating portion 310, a transition portion 320 and a base portion 330. The split ring electrode 300 may be unitarily formed from a metal, alloy, conductive oxide, or any other suitable conductive material. Alternatively, the split ring electrode 300 may be formed of distinct segmented that are subsequently coupled using welding or other suitable methods.

As seen in FIG. 3A, the stimulating portion 310 of the split ring electrode 300 may be formed in the shape of a portion of a cylinder. The size and shape of the stimulating portion 310 will depend on the number of the split ring electrodes 300 that will be used and the configuration in which they will be used. In some embodiments, the cross-section of the stimulating portion 310 creates a semi-cylindrical portion, though it will be understood that the stimulating portion 310 may encompass any part of a cylinder, such as one-quarter, one-third, or two-thirds of a cylinder. In at least some embodiments, the arc length of the stimulating portion 310 encompasses a portion of a circle that is smaller than the reciprocal of the number of split ring electrodes 300 that will be used at a given level. For example, if three split ring electrodes 300 are disposed at a given longitudinal level, then the arc length of the stimulating portion of each split ring electrode may be less than one-third of a circle (i.e. less than 120 degrees). Thus, the sum of the arc lengths of the stimulating portions 310 will not equal 360 degrees so that gaps are formed between adjacent stimulating portions 310. These gaps will separate the stimulating portions 310 from one another and allow the stimulating electrodes 310 to function independently.

The split ring electrode 300 also includes a base portion 330. The base portion 330 may be formed from the same material as the stimulating portion 310 (e.g. a metal, alloy, conductive oxide, or other conductive material). Alternatively, the base portion 330 may be formed of a non-conductive material that is coupleable to the stimulating portion 310 through the use of a transition portion 320 as will be described below or through any other suitable method. As seen in FIG. 3A, the base portion 330 may be formed in a shape similar to the stimulating portion 310. In some embodiments, the base portion 330 has a cross-section in the shape of a portion of a cylinder. The arc-length of this base portion 330 may be the same, greater than or less than that of the corresponding stimulating portion 310. Furthermore, the radius of curvature of the stimulating portions 310 may be larger than that of the base portions 330. As will be appreciated by one of ordinary skill in the art, the length, width and thickness of the base portion 330 and stimulating portion 310 may also be the same or different as desired. For example, in some embodiments, the base portion 330 is formed thicker than the stimulating portion 310 for overall reinforcement of the structure.

Figure 3B:
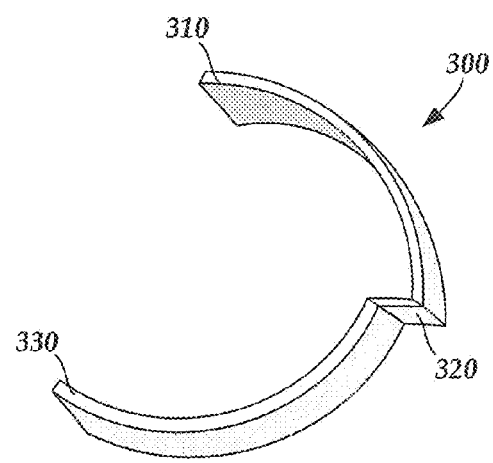
FIG. 3B is a schematic perspective view of another embodiment of a split ring electrode, according to the invention.

A transition portion 320 may be formed between the stimulating portion 310 and the base portion 330. In at least some embodiments, the transition portion 320 is configured to allow the interlocking of the plurality of split ring electrodes 300 as will be described in greater detail below with reference to FIG. 5. In some embodiments, the transition portion 320 is a slightly curved member that serves to join the stimulating portion 310 and the base portion 330. FIG. 3B is a schematic perspective view of another embodiment of a split ring electrode 300. As can be appreciated from FIG. 3B, the transition portion 320 may instead be formed of a substantially straight member that connects the stimulating portion 310 and the base portion 330. It will be understood that the angle and length of the transition portion 320 may be modified.

Figure 3C:
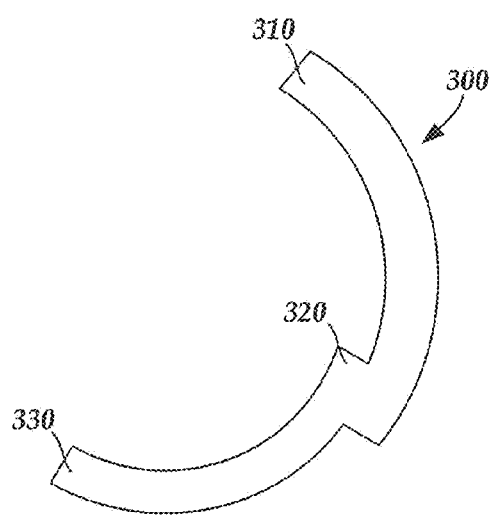
FIG. 3C is a schematic cross-sectional view of the split ring electrode of FIG. 3B, according to the invention.

FIG. 3C is a schematic cross-sectional view of the split ring electrode of FIG. 3B. The split ring electrode 300 may be configured in a way such that the overall cross-sectional shape of the split ring electrode 300 resembles two portions of a cylinder assembled end-to-end at a transition portion 320. In embodiments where the split ring electrode 300 is formed from one unitary piece, the shape of the split ring electrode 300 may be provided by stamping the piece into the appropriate shape, although alternatively other methods of manufacture may be used. Manufacturing the split ring electrodes 300 from a stamped unitary piece may be useful in reducing both the cost and the possibility of an electrode breakage or failure. In at least some other embodiments, the transition portion 320 serves to couple a conductive stimulating portion 310 with a nonconductive base portion 330.

Figure 4:
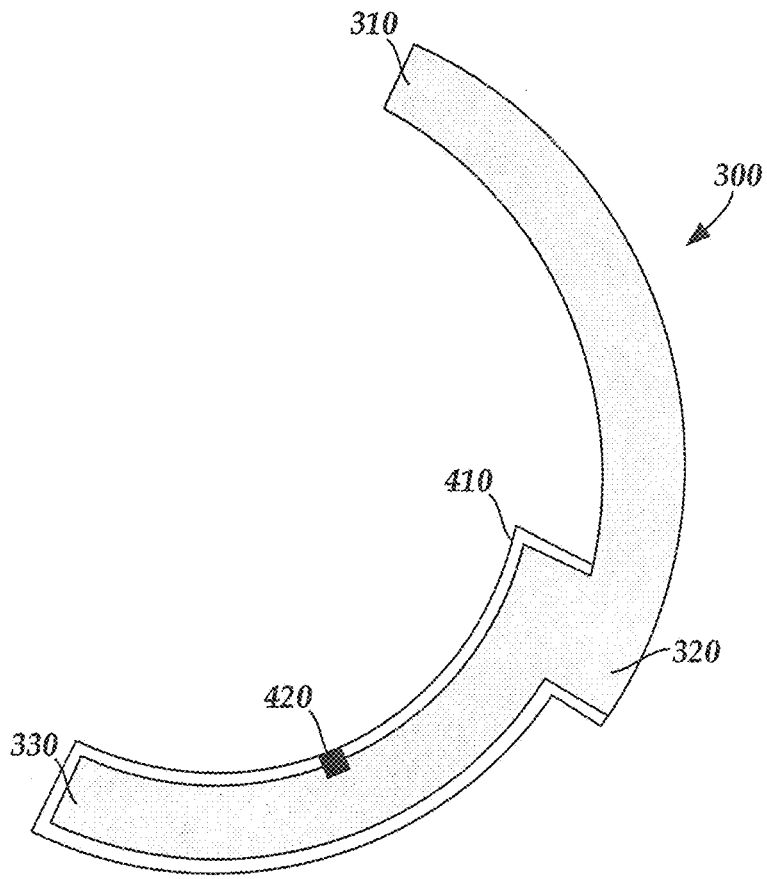
FIG. 4 is a schematic cross-sectional view of one embodiment of a split ring electrode having an insulative coating, according to the invention.

An insulative coating may be applied to the split ring electrodes 300 to electrically insulate them from one another. FIG. 4 is a schematic perspective view of one embodiment of a split ring electrode 300 having an insulative coating 410. As seen in FIG. 4, in some embodiments, the base portion 330 is coated with an insulative coating 410. The insulative coating 410 may include any suitable insulator such as, for example, silicone, polyurethane, polyetheretherketone, polysulfone, nylon, polytetrafluoroethylene (e.g., Teflon®), or some other implant grade non-conductive material. In the case of silicone and certain other insulators, the insulative coating 410 may be applied using a dip molding process or any other suitable method. As previously indicated, applying an insulative coating 410 to the base portion 330 may be useful in electrically separating one split ring electrode 300 from an adjacent split ring electrode 300.

In some embodiments, the insulative coating 410 covers the entirety or a substantial portion of the base portion 330. Preferably, the insulative coating 410 is applied to cover a portion of the base portion 330 that would otherwise be in contact with a stimulating portion 310 of an adjacent split ring electrode 300. In at least some embodiments, the insulative coating 410 is applied to both the base portion 330 and the transition portion 320. Alternatively, the insulative coating 410 may be applied to only part of the transition portion 320 or to only one side of the transition portion 320. The bottom of the base portion 330, or a part of the base portion 330 might not be insulated.

A conductor (e.g. a wire) 420 may be attached to any portion of the split ring electrode 300. As seen in FIG. 4, a conductor 420 may be attached to the base portion 310 of the split ring electrode 300. Thus, in some embodiments, a piece of the insulative coating 410 may be removed so that that conductor 420 can properly attach to the base portion 310 of the split ring electrode 300. Any method of removing a fragment of the insulative coating 410 may be used. In some embodiments, an ablation process is used to remove a part of the insulative coating 410 so that a conductor 420 may be welded to the base portion 330. Alternatively, the conductor 420 may be coupled to the transition portion 320 or the stimulating portion 330. If the transition portion 320 is coated with an insulative coating 410, portions of the insulative coating 410 may need to be removed as described herein.

Figure 5:
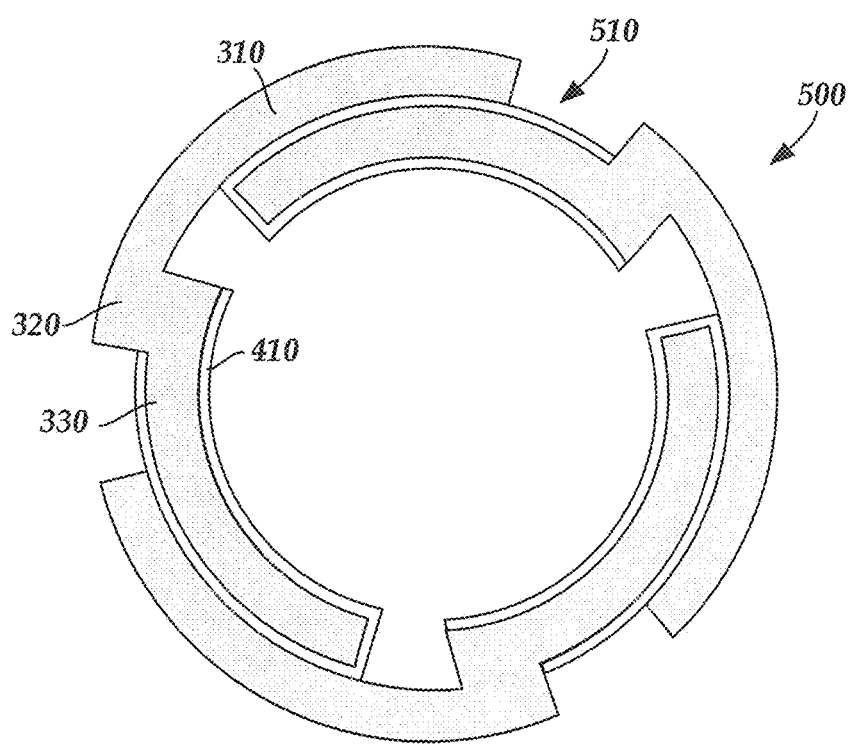
FIG. 5 is a schematic cross-sectional view of a plurality of split ring electrodes arranged in a ring array, according to the invention.

FIG. 5 is a schematic cross-sectional view of a plurality of split ring electrodes 300 arranged in a ring array. In this illustrated embodiment, three split ring electrodes 300 are assembled into a ring array 500. As seen in FIG. 5, the split ring electrodes 300 may be positioned such that the base portion 330 of one split ring electrode 300 is disposed underneath or radially inward of the stimulating portion 310 of a split ring electrode 300 that is adjacent to the first in the counter-clockwise direction. It will be appreciated from the cross-section of the ring array 500 that the result of this arrangement define two concentric cylinders. The first cylinder is disposed on the inside of the ring array 500 and includes only the base portions 330 of the plurality of split ring electrodes 300. A second concentric cylinder is formed over the first cylinder. The second cylinder is formed of the stimulating portions 310 of the plurality of split ring electrodes 300. In some embodiments, the first cylinder is formed to have a radius equal to or slightly larger than the diameter of the lead body on which it will be disposed.

In some embodiments, it will be desirable to electrically insulate the plurality of split ring electrodes 300 from each other. As can be appreciated from FIG. 5, the insulative coating 410 serves to insulate the base portion 330 of each of the split ring electrodes 300 from the stimulating portions 310 of the adjacent split ring electrodes 300. Furthermore, as briefly described above, gaps 510 may be formed between the stimulating portions so that they are electrically insulated from one another. If an insulative coating 410 is applied to the transition portions 320, the stimulating portions 310 may be extended so that they abut one another with the insulative coating 410 providing the desired insulation between the two stimulating portions 310. Furthermore, it will be understood that the overlap between the base portion 330 of one split ring electrode 300 and a stimulating portion 310 of an adjacent split ring electrode 300 may vary. For example, in some embodiments, the base portion of 330 of one split ring electrode 300 and the stimulating portion 310 of an adjacent split ring electrode 300 cover the same radial angle and fully overlap (i.e. the base portion 330 overlaps about 95% of the stimulating portion 310). In other embodiments, the base portion 330 overlaps up to 99% of the stimulating portion 310. In other embodiments, the base portion 330 overlaps up to 90% of the stimulating portion 310. In other embodiments, the base portion 330 overlaps up to 80% of the stimulating portion 310. In other embodiments, the base portion 330 overlaps up to 75% of the stimulating portion 310. In other embodiments, the base portion 330 overlaps up to 60% of the stimulating portion 310. In other embodiments, the base portion 330 overlaps up to 50% of the stimulating portion 310.

Though FIG. 5 illustrates a ring array 500 having three split ring electrodes 300, any number of split ring electrodes 300 may be used to form the ring array 500. As few as two split ring electrodes 300 may be used to form a ring array 500. In some embodiments, the ring array 500 is formed using two, three, four, five, six, eight, ten, or twelve split ring electrodes 300. The split ring electrodes 300 of any given ring array 500 may be of the same size and shape or they may have different sizes and/or shapes. For example, the stimulating portions 310 of the split ring electrodes 300 may be of the same length or of different lengths in a ring array 500.

Furthermore, it will be understood that a lead may include any number of ring arrays 500. Each ring array 500 may be configured the same or differently than one or more of the others. For example, a lead may include a ring array 500 having three split ring electrodes 300 at a first level, a second ring array 500 having three split ring electrodes 300 at a second level and a third ring array 500 having two split ring electrodes 300 at a third level to form a lead having a 3-3-2 configuration as described above. Thus, at least one ring array 500 may be formed to have a different configuration than the others as desired. Additionally, ring electrodes 130 may be disposed between ring arrays 500 in positions where segmented electrodes are not necessary. In some embodiments, the stimulating portions 310 of different ring arrays 500 are radially aligned. In at least some embodiments, stimulating portions 310 of different ring arrays 500 are radially offset.

The interlocking and mutually supporting configuration of the ring array 500 allows for sturdy electrode construction. This configuration allows each split ring electrode 300 to support and secure the adjacent electrode. By forming leads using ring arrays 500 it may be possible to reduce the possibility of lead failure and breakage. Specifically, leads manufactured using ring arrays 500 are less prone to failure because the stimulating portions 310 are secured by the base portions 330. Thus, electrodes are less prone to detachment and disconnection from the lead body.

Figure 6:
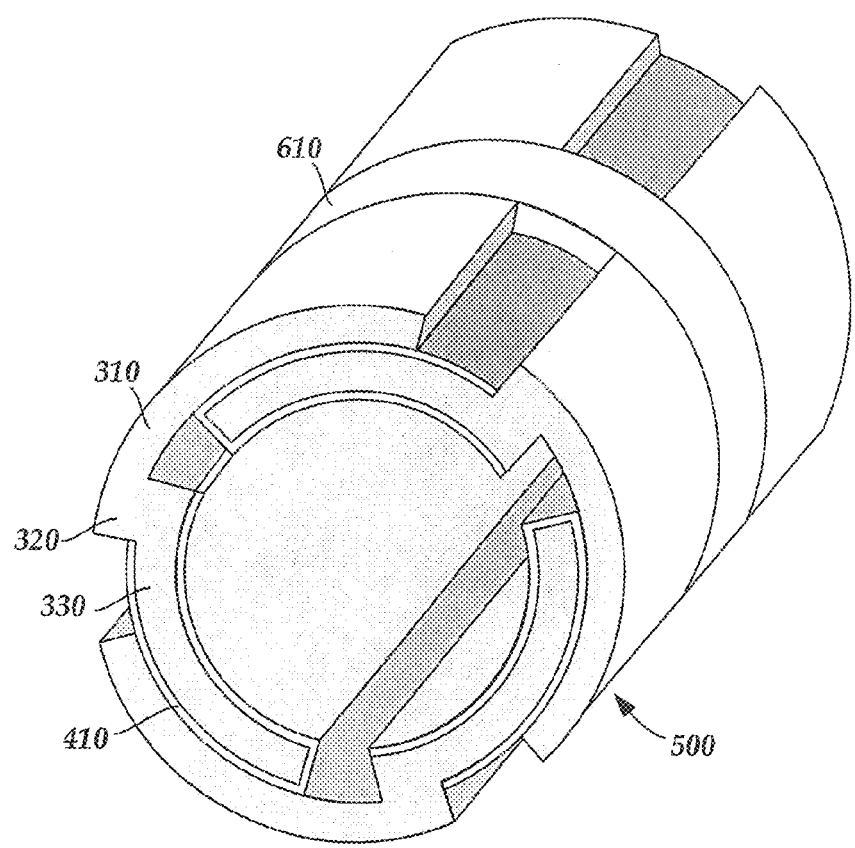
FIG. 6 is a schematic perspective view of a plurality of ring arrays and a spacer, according to the invention.

FIG. 6 is a schematic perspective view of the plurality of split ring electrodes 300 and a spacer 710. The split ring electrodes 300 are arranged into two ring arrays 500 as described above. In some embodiments, spacers 610 are placed to control the distance between the ring arrays 500 and to electrically insulate one ring array 500 from another. The spacer 610 may be in the form of a short cylinder or ring that separates the two rings arrays 500 as illustrated in FIG. 6. The spacers 610 may be formed of any suitable non-conductive material capable of electrically insulating the stimulating portions 310 of the split ring electrodes 300. Additionally, in embodiments having gaps 510, the same material used to form the spacers 610 may be used to form a longitudinal spacer between the individual split ring electrodes 300. It will be understood that the size and shape of the spacers may be varied to separate the ring arrays 500 as desired. For example, in some embodiments, the spacers 610 have the same longitudinal width as the ring arrays 500. Alternatively, the spacers 610 may be wider or narrower in the longitudinal direction than the ring arrays 500. The spacers 610 may also have the same diameter as the ring arrays 500 in order to produce an isodiametric lead.

After manufacture of the individual components, the spacers 610 and ring arrays 500 may be coupled to a lead body using any suitable method. In some embodiments, the plurality of split ring electrodes 300 are coupled to create ring arrays 500, and the ring arrays 500 are then slid onto a lead body where they will be permanently secured using welding, or a suitable adhesive. The spacers 610 may also be slid onto the lead body between the ring arrays 500.

Because the split ring electrodes 300 may be manufactured separately, in some embodiments it may be useful to have additional methods of aligning them. For example, to form the ring array 500 described above, each of the split ring electrodes 300 must be disposed in the proper position and orientation. Proper alignment of the split ring electrodes 300 may be accomplished using alignment tabs as will be described with reference to FIG. 7.

Figure 7:
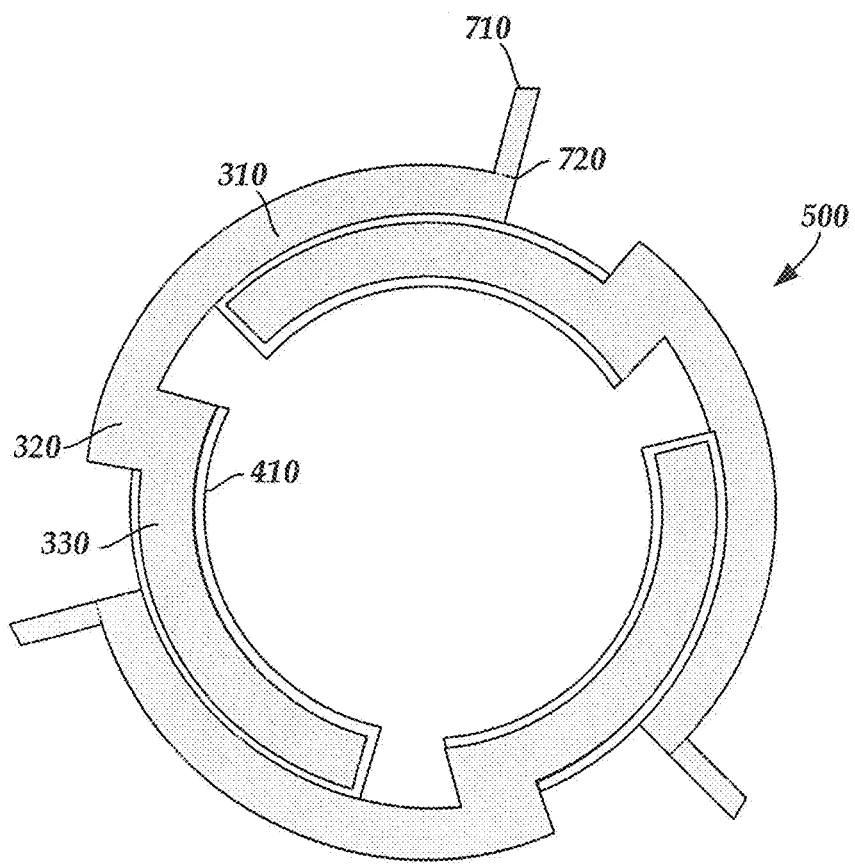
FIG. 7 is a schematic cross-sectional view of one embodiment of a plurality of split ring electrodes having alignment tabs, according to the invention.

FIG. 7 is a schematic cross-sectional view of one embodiment of a ring array having alignment tabs 710. The alignment tabs 710 may be in the form of projecting flaps, extensions, tips, or handles. As seen in FIG. 7, in some embodiments, an alignment tab 710 is coupled to the stimulating portion 310 of each of the split ring electrodes 300. Alternatively, the alignment tabs 710 may be unitarily formed with the stimulating portion 310 in the form of an outwardly bent top portion. The alignment tabs 710 may also be coupled to or formed of a portion of the transition portion 320 or even the base portion 330. It will be understood that the location and the form of the alignment tab 710 may be modified so long as the structure is able to orient and manipulate the split ring electrode 300 into a desired position. Using the alignment tabs 710, it may be possible to maintain the gaps 510 between the split ring electrodes 300.

In some embodiments, the base of the alignment tabs 710 may be connected to the stimulating portion 310, the transition portion 320 or the base portion 330 and form a notched portion 720. The notched portion 720 may be configured in any suitable manner that forms a scored or weakened joint or seam between the alignment tab 710 and the split ring electrode 300. The use of a notched portion 720 is useful if it is desirable to remove the alignment tabs 710 after proper alignment. In this manner, the alignment tabs 710 may simply be broken off the split ring electrodes 300 after alignment. Alternatively, the tabs 710 can be ground down or cut.

Figure 8:
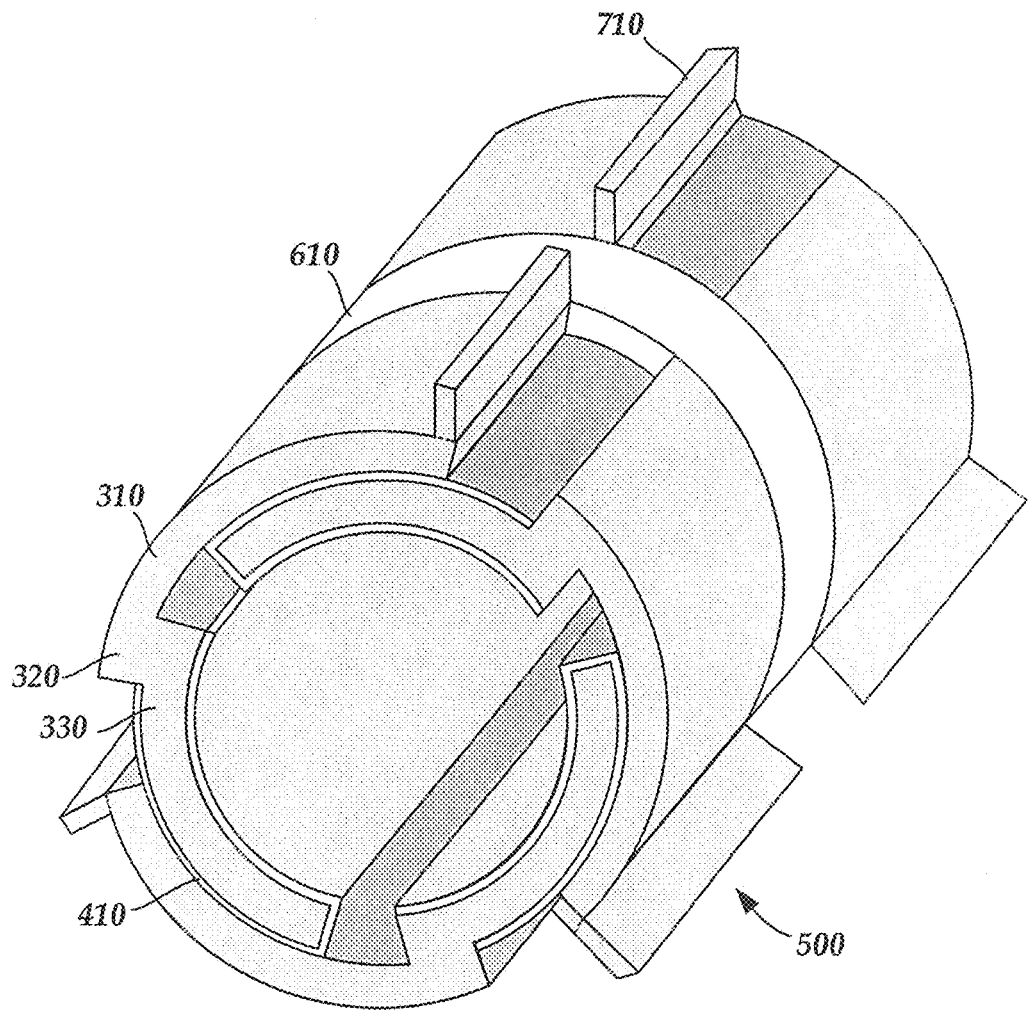
FIG. 8 is a schematic perspective view of a plurality of ring arrays having alignment tabs and separated by a spacer, according to the invention.

FIG. 8 is a schematic perspective view of the plurality of split ring electrodes having alignment tabs and separated by a spacer. As seen in FIG. 8, the alignment tabs 710 may be used to position the plurality of split ring electrodes 300 into a ring array 500 having gaps 510. Additionally, the alignment tabs 710 may also be useful in positioning one ring array 500 with respect to a second ring array 500. For example, FIG. 8 illustrates two ring arrays 500 that are radially aligned (i.e. the base portions 330, transition portions 320, stimulating portions 310 and alignment tabs 710 of each are radially aligned). One of ordinary skill in the art may quickly appreciate that the ring arrays 500 are radially aligned by observing the positions of the alignment tabs 710. Additionally, if a staggered orientation is desired, the alignment tabs 710 may be used to rotate one of the ring arrays 500 about the lead body so that the alignment tabs 710 of one ring array 500 are not in line with the alignment tabs 710 of a second ring array 500.

Figure 9A:
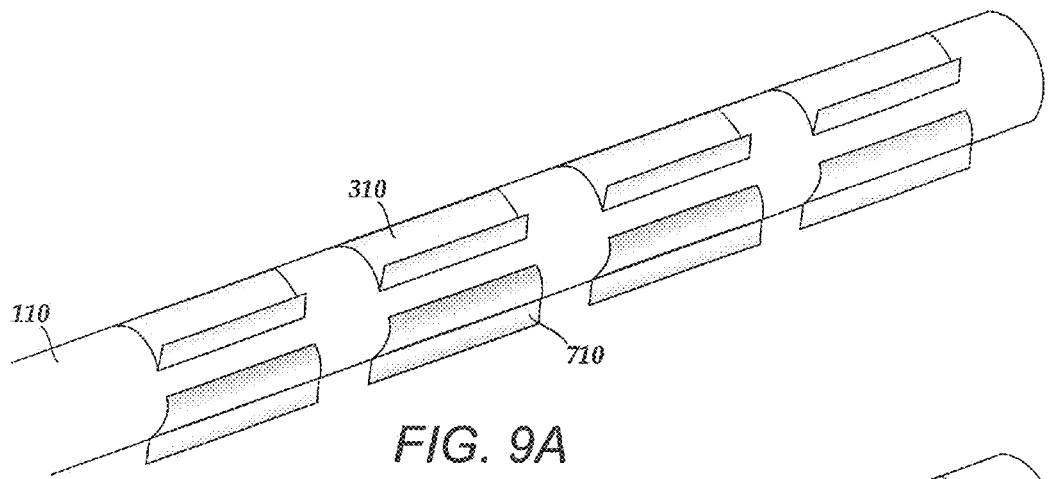
FIG. 9A is a schematic perspective view of one embodiment of a portion of a lead having a plurality of split ring electrodes and alignment tabs, according to the invention.
Figure 9B:
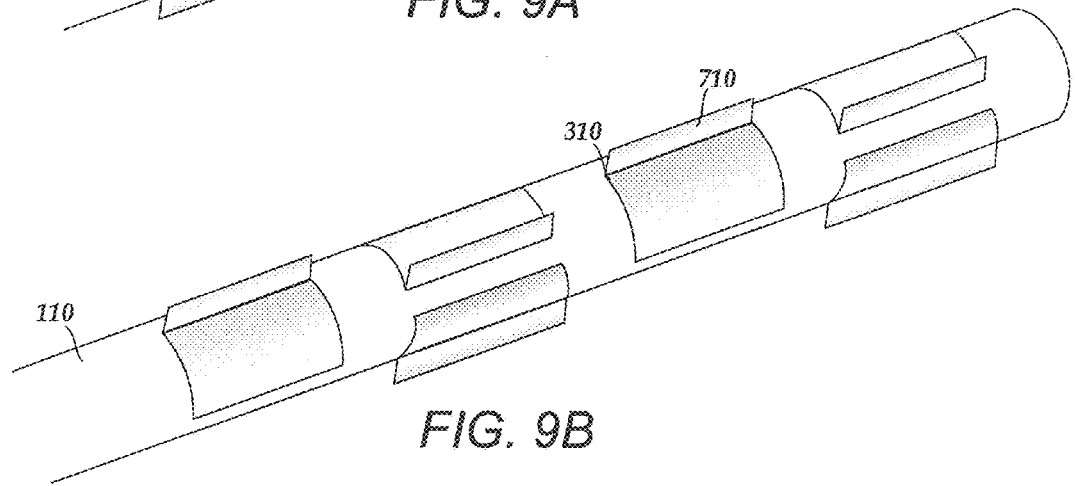
FIG. 9B is a schematic perspective view of another embodiment of a portion of a lead having a plurality of split ring electrodes and alignment tabs arranged in a staggered orientation, according to the invention.

FIG. 9A is a schematic perspective view of one embodiment of a portion of a lead having a plurality of split ring electrodes and alignment tabs. With the alignment tabs 710 radially aligned, a lead similar to that earlier described in FIG. 1A may be formed. However, if a staggered configuration is preferable, the alignment tabs 710 of one ring array 500 may be used to rotate the ring array 500 into the staggered position. It will be understood that rotation of the ring array 500 may also be accomplished without using the alignment tabs 710. FIG. 9B is a schematic perspective view of one such embodiment of a portion of a lead having a plurality of split ring electrodes and alignment tabs arranged in a staggered orientation.

Figure 9C:
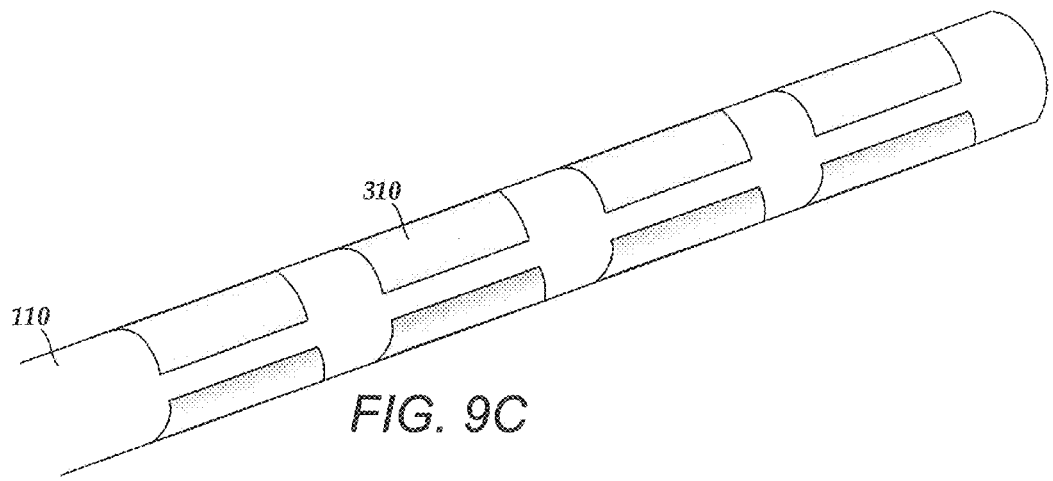
FIG. 9C is a schematic perspective view of the portion of the lead of FIG. 9A after grinding of the alignment tabs, according to the invention.

Thus, the ring arrays 500 and the spacers 610 may be correctly positioned in the longitudinal direction and properly radially aligned. Furthermore, using a welding technique, or a suitable adhesive, the ring arrays 500 and the spacers 610 may be permanently secured to the lead body 110. The alignment tabs 710 may then be removed if an isodiametric lead is desired. In some embodiments, the alignment tabs 710 are simply broken off at the notched portion 720. In at least some other embodiments, the lead having ring arrays 500 and spacers 610 may be ground to the appropriate diameter. FIG. 9C is a schematic perspective view of the portion of a lead of FIG. 9A after grinding or otherwise removing the alignment tabs 710. In some embodiments, the alignment tabs 710 will be removed by grinding the assembled lead, though it will be understood that any other suitable method may be used to remove the alignment tabs 710.

Modifications of these methods are possible. For example, though the stimulating portions 310 may need to be formed of a conductive material, other materials may be used in forming the base portions 330 and the transition portions 320. Furthermore, by varying the size and shape of the split ring electrodes 300, it may be possible to produce leads having different stimulation and recording advantages. In some embodiments, these methods are used with lead constructions other than deep brain stimulation leads.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A device for brain stimulation, comprising:
 a lead body having a longitudinal surface and a distal end;
 at least one ring array comprising at least three split ring electrodes disposed on the distal end of the lead body, each of the at least three split ring electrodes comprising a stimulating portion and a base portion coupled to the stimulating portion, the stimulating portion extending around a portion of the circumference of the lead body and the base portion extending in a circumferential direction away from the stimulating portion, the base portion and the stimulating potion each comprising a top surface and a bottom surface opposite the top surface, wherein the split ring electrodes of the at least one ring array are arranged about the circumference of the lead body, and wherein at least a portion of the base portion of each of the at least three split ring electrodes is disposed radially below, and insulated from, at least a portion of the stimulating portion of an adjacent one of the at least three split electrodes, wherein the top surface of the stimulating portion comprises at least a section of a circle having a first radius and the top surface of the base portion comprises at least a section of a second circle having a second radius, the first radius being greater than the second radius; and an insulative material disposed between the at least three split ring electrodes and disposed directly on top of the top surface of the base portion of each of the at least three split ring electrodes and directly underneath the bottom surface of the stimulating portion of each of the at least three split electrodes;

wherein the device is configured and arranged for brain stimulation.

2. The device of claim 1, wherein each at least one ring array comprises exactly three spit ring electrodes.

3. The device of claim 1, wherein each of the at least one ring array comprises at least four split ring electrodes.

4. The device of claim 1, wherein the insulative material comprises an insulative coating directly on the top surface of the base portion of each of the at least three split ring electrodes.

5. The device of claim 4, wherein the insulative coating is applied using a dip-molding process.

6. The device of claim 1, wherein the at least three split rings electrodes are disposed on the lead body so that the device is isodiametric.

7. The device of claim 1, further comprising at least one spacer disposed adjacent to one of the at least one ring array.

8. The device of claim 1, further comprising plurality of conductors coupled to the at least three split ring electrodes.

9. The device of claim 1, wherein the device comprises at least two ring arrays, wherein the stimulating portions of the split ring electrodes of a one of the ring arrays are aligned with the stimulating portions of the split ring electrodes of another of the ring arrays.

10. The device of claim 1, wherein the device comprises at least two ring arrays, wherein the stimulating portions of the split ring electrodes of a one of the ring arrays are offset from the stimulating portions of the split ring electrodes of another of the ring arrays.

11. The device of claim 1, wherein a portion of the insulative material is disposed directly between the top surface, of the base portion of a one of the split ring electrodes and the bottom surface of the stimulating portion of another one of the split ling electrodes.

12. The device of claim 1, wherein a portion of the insulative material is disposed radially between the top surface of the base portion of a one of the split ring electrodes and the bottom surface of the stimulating portion of another one of the split ring electrodes.

13. A device for brain stimulation, comprising:
a lead body having a longitudinal surface and a distal end;
at least three split ring electrodes disposed on the distal end of the lead body, each of the at least three split ring electrodes comprising a stimulating portion and a base portion coupled to the stimulating portion, the stimulating portion extending around a portion of the circumference of the lead body and the base portion extending in a circumferential direction away from the stimulating portion, the base portion and the stimulating potion each comprising a top surface and a bottom surface opposite the top surface; and an insulative material disposed between the at least three split ring electrodes and disposed directly on top of the top surface of the base portion of each of the at least three split ring electrodes and directly underneath the bottom surface of the stimulating portion of each of the at least three split electrodes, wherein the split ring electrodes are arranged such that the top surfaces of the base portions are arranged around an inner circle having a first radius and the top surfaces of the stimulating portions are arranged around an outer circle having a second radius, wherein the first radius is less than the second radius, wherein the device is configured and arranged for brain stimulation.

14. The device of claim 13, wherein the inner circle and the outer circle are concentric.

15. The device of claim 13, wherein a portion of the insulative material is disposed directly between the top surface of the base portion of a one of the split ring electrodes and the bottom surface of the stimulating portion of another one of the split ring electrodes.

16. An implantable stimulation device, comprising:
the device of claim 1; and
a control module coupleable to the lead.

17. The implantable stimulation device of claim 16, wherein the implantable stimulation device is a deep brain stimulator.

18. A method of manufacturing a device for brain stimulation, the method comprising:
forming a lead body having a longitudinal surface and a distal end; and
forming at least one ring array comprising at least three split ring electrodes at the distal end of the lead body, each of the at least three split ring electrodes comprising a stimulating portion and a base portion coupled to the stimulating portion, the stimulating portion extending around a portion of the circumference of the lead body and the base portion in a circumferential direction away from the stimulating portion, the base portion and the stimulating portion each comprising a top surface and a bottom surface opposite the top surface, wherein the split ring electrodes of the at least one ring array are arranged about the circumference of the lead body and wherein at least a portion of the base portion of each of the of at least three split ring electrodes is disposed radially below and insulated from, at least a portion of the stimulating portion of an adjacent one of the at least three split electrodes by an insulative material disposed between the at least three split ring electrodes and disposed directly on top of the top surface of the base portion of each of the at least three split ring electrodes and directly underneath the bottom surface of the stimulating portion of each of the at least three split electrodes, wherein the device is configured and arranged for brain stimulation.

19. The method of claim 18, wherein each of the split ring electrodes comprises at least one alignment tab extending radially outward from the stimulation portion of the split ring electrode, the method further comprising aligning the at least one ring array using the alignment tabs.

20. The method of claim 19, further comprising grinding the alignment tabs so that the lead body and the at least three split ring electrodes are isodiametric.

* * * * *